US011918552B2

(12) United States Patent
Rossolini et al.

(10) Patent No.: US 11,918,552 B2
(45) Date of Patent: Mar. 5, 2024

(54) N-ACETYLCYSTEINE FOR USE AS ANTIBACTERIAL AGENT

(71) Applicant: Zambon S.P.A., Bresso (IT)

(72) Inventors: Gian Maria Rossolini, Siena (IT); Lucia Pallecchi, Colle di Val d'Elsa (IT); Francesco Sergio, Piacenza (IT)

(73) Assignee: Zambon S.P.A., Bresso (IT)

( * ) Notice: Subject to any disclaimer, the term of this patent is extended or adjusted under 35 U.S.C. 154(b) by 135 days.

(21) Appl. No.: 17/134,719

(22) Filed: Dec. 28, 2020

(65) Prior Publication Data

US 2021/0113508 A1 Apr. 22, 2021

Related U.S. Application Data

(62) Division of application No. 16/468,716, filed as application No. PCT/EP2017/082512 on Dec. 13, 2017, now abandoned.

(30) Foreign Application Priority Data

Dec. 15, 2016 (EP) .................................... 16204412

(51) Int. Cl.
*A61K 31/197* (2006.01)
*A61P 31/04* (2006.01)

(52) U.S. Cl.
CPC ............ *A61K 31/197* (2013.01); *A61P 31/04* (2018.01)

(58) Field of Classification Search
CPC .................................................. A61K 31/165
See application file for complete search history.

(56) References Cited

U.S. PATENT DOCUMENTS 6,475,434 B1 * 11/2002 Darouiche ............. A61L 31/08
422/35
2014/0243304 A1    8/2014 Montgomery

FOREIGN PATENT DOCUMENTS

| CA | 2662636 A1 | 10/2009 | |
| JP | 2012522037 A | 9/2012 | |
| WO | 2002078627 A2 | 10/2002 | |
| WO | WO-2004000298 A1 * | 12/2003 | ........... A61K 31/165 |
| WO | 2011128230 A1 | 10/2011 | |
| WO | 2014191410 A1 | 12/2014 | |
| WO | 2016120787 A1 | 8/2016 | |

OTHER PUBLICATIONS

Zou (Modern Preventive Medicine vol. 43 pp. 1287-1290. Published Apr. 2016). (Year: 2016).*
Brooke (Stentrophomas Maltophilia: An emerging global opportunistic pathogen. Clinical Microbiology Reviews pp. 2-41 published 2012) (Year: 2012).*
Mullen (Microbial Pathogenesis vol. 49 pp. 381-397 published 2010). (Year: 2010).*
Letter issued on May 26, 2021 reporting office action issued by Eurasian Patent Office.
Office Action dated Mar. 25, 2021 issued in counterpart application No. 201991331 by Eurasian Patent Office.
Tse H.N. et al., "High-dose N-acetylcysteine in stable COPD," Chest, 2013; 144(1):106-118.
Letter reporting office action issued by Colombian Patent Office on Feb. 11, 2022 in connection with Colombian patent application No. NC2019/0006311.
Office Action dated Feb. 11, 2022 in connection with counterpart Colombian patent application n.: NC2019/0006311.
Zhao T. et al., "N-acetylcysteine inhibit biofilms produced by Pseudomonas aeruginosa", BMC Microbiology 2010, 10:140 pp. 1-8.
Blasi F., et al., "The effect of N-acetylcysteine on biofilms: Implications for the treatment of respiratory tract Infections", Respiratory Medicine, London, GB, vol. 117, Jun. 16, 2016, pp. 190-197.
Brooke J.S., "Stenotrophomonas maltophilia: an Emerging Global Opportunistic Pathogen", Clinical Microbiology Reviews, pp. 2-41, 2012.
Cedric C., et al., "Cysteamine (Lynovex?), a novel mucoactive antimicrobial & antibiofilm agent for the treatment of cystic fibrosis", Orphanet Journal of Rare Diseases, Biomed Central Ltd, L0, vol. 9, No. 1, Nov. 30, 2014, p. 189.
International Search Report of PCT/EP2017/082512 dated Mar. 20, 2018.
Landini G., et al., "Effect of high N-acetylcysteine concentrations on antibiotic activity against a large collection of respiratory pathogens", Antimicrobial Agents and Chemotherapy, Dec. 2016, vol. 60, No. 12, pp. 7513-7517.
Written Opinion of the International Searching Authority dated Mar. 20, 2018.
Zou Y-M et al., "Bacteriostasis effect of N-acetyl cysteine in common respiratory pathogens and its influencing factors", Modern Preventive Medicine, vol. 43, pp. 1287-1290, 2016.
El-Rehewy M.S.K. et al., In vitro efficacy of ureteral catheters impregnated with ciprofloxacin, N-acetylcysteine and their combinations on microbial adherence.
Letter received from Colombian Foreign Agent reporting office action issued with regard to application No. NC2019/0006311.
Office Action issued dated Jul. 29, 2022 in connection with counterpart Columbian patent application No. NC2019/0006311.
Letter dated Feb. 6, 2023 of Colombian associate reporting office action issued in counterpart Colombian application No. NC2019/0006311.
Office Action dated Dec. 9, 2022 in connection to counterpart Colombian patent application No. NC2019/0006311.
Office Action dated Aug. 8, 2023 in counterpart European Application No. 21163647.7-1112.

* cited by examiner

*Primary Examiner* — Theodore R. Howell
*Assistant Examiner* — George W Kosturko
(74) *Attorney, Agent, or Firm* — SILVIA SALVADORI, P.C.; Silvia Salvadori

(57) ABSTRACT

The present invention relates to N-acetylcysteine for the use in the treatment of bacterial infections caused by a pathogen selected from *Burkholderia cepacia* complex (BCC) and *Stenotrophomonas maltophilia* (*S. maltophilia*) strains.

9 Claims, No Drawings

N-ACETYLCYSTEINE FOR USE AS ANTIBACTERIAL AGENT

This Application is a Divisional Application of U.S. Ser. No. 16/468,716 filed on Jun. 12, 2019, which is a U.S. national stage of PCT/EP2017/082512 filed on 13 Dec. 2017, which claims priority to and the benefit of European Patent Application No. 16204412.7, filed on 15 Dec. 2016, the contents of which are incorporated herein by reference in their entirety.

FIELD OF THE INVENTION

The present invention relates to N-acetylcysteine (hereinafter NAC) for use in inhibiting or suppressing the growth of and/or killing of susceptible strains of pathogens selected from *Burkholderia cepacia* complex (hereinafter BCC) and *Stenotrophomonas maltophilia* (hereinafter *S. maltophilia*).

More in particular, the present invention relates to NAC for use in the treatment of a disease caused at least in part by a pathogen selected from BCC and *S. maltophilia* strains.

BACKGROUND OF THE INVENTION

BCC poses little medical risk to healthy people. However, the respiratory tract of individuals with weakened immune systems or chronic lung disease, particularly cystic fibrosis, may be more susceptible to BCC infections. Infections by BCC can cause pulmonary exacerbations accelerating decline in lung functions, for example in cystic fibrosis patients.

As a chronic colonizer, BCC may also cause infections in patients with lung disease other than cystic fibrosis, such as chronic obstructive pulmonary disease and chronic granulomatous disease.

*S. maltophilia* infections occur principally, but not exclusively, in debilitated and immunosuppressed individuals. *S. maltophilia* is commonly associated with respiratory tract infections in humans; for example, *S. maltophilia* can trigger pulmonary exacerbations of chronic obstructive pulmonary disease and cystic fibrosis.

Both BCC and *S. maltophilia* are characterized by a multidrug resistance phenotype and the ability to form biofilms. In virtue of this features, they are responsible for chronic lung colonization in individuals with weakened immune systems or chronic lung disease, particularly cystic fibrosis, which may last several months or years and are difficult or impossible to be eradicated by current antibiotic treatment strategies.

SUMMARY OF THE INVENTION

The Applicant perceived that the occurrence of BCC and *S. maltophilia* infections can result in episodes of pulmonary exacerbation worsening the already compromised clinical conditions of the individuals affected by chronic diseases impacting also the lower respiratory system such as, e.g. cystic fibrosis and chronic obstructive pulmonary disease.

Accordingly, the Applicant has faced the problem of treating BCC and/or *S. maltophilia* infections, which cause at least in part episodes of pulmonary exacerbation in individuals suffering of a chronic disease impacting also the lower respiratory system such as, e.g. cystic fibrosis and chronic obstructive pulmonary disease.

After a long set of tests and experimentations, the Applicant has surprisingly found that NAC is able to exert an antimicrobial activity against a consistent number of BCC and *S. maltophilia* clinical isolates, even resulting in a bactericidal effect. Even more strikingly, NAC has been found to have anti-biofilm activity in in vitro biofilm models of BCC and *S. maltophilia*. NAC may be therefore envisaged as a therapeutic tool useful in the treatment of BCC and/or *S. maltophilia* infections, so contributing to conditions improvement of patients having a clinical picture severely compromised, such as the above-mentioned patients. The ability of NAC in inhibiting the formation of BCC and/or *S. maltophilia* biofilms envisages a potential use also for preventing lung colonization by those pathogens, especially in the individuals affected by chronic diseases impacting also the lower respiratory system such as, e.g. cystic fibrosis and chronic obstructive pulmonary disease.

DETAILED DESCRIPTION OF THE INVENTION

NAC is the acetylated precursor of both the amino acid L-cysteine and reduced glutathione (GSH). Historically it has been used as a mucolytic agent in conjunction with chest physiotherapy in patients who have viscid or thickened airway mucus for a range of chronic respiratory illnesses, as an antidote due to acetaminophen overdose ad as a potential treatment of diseases characterized by free radical, oxidant damage.

In accordance with the present invention, the Applicant has now been surprisingly discovered that NAC is also effective in inhibiting or suppressing the growth and/or killing susceptible strains of BCC and *S. maltophilia*, known to be at least in part responsible of episodes of pulmonary exacerbation, worsening the already compromised clinical conditions in individuals affected by chronic diseases impacting also the lower respiratory system such as, e.g. cystic fibrosis and chronic obstructive pulmonary disease.

It is therefore an object of the present invention NAC for use in inhibiting or suppressing the growth and/or killing a susceptible strain of a pathogen selected from BCC and *S. maltophilia*.

It is another object of the present invention NAC for use in the treatment of a bacterial infection caused by a susceptible strain of a pathogen selected from BCC and *S. maltophilia*.

It is a further object of the present invention NAC for use in the treatment of episodes of pulmonary exacerbations caused at least in part by a susceptible strain of a pathogen selected from BCC and *S. maltophilia*, in an individual suffering of a chronic disease impacting also the lower respiratory system, such as, e.g. cystic fibrosis and chronic obstructive pulmonary disease.

In a particular aspect of the present invention, individuals suffering of a chronic disease as described above are immunocompromised and/or hospitalized patients.

In another aspect, the present invention relates to NAC for use in inhibiting the formation of BCC and/or *S. maltophilia* biofilms and, especially, NAC for use in preventing lung colonization by in inhibiting the formation of BCC and/or *S. maltophilia* biofilms, particularly in the individuals affected by chronic diseases impacting also the lower respiratory system such as, e.g. cystic fibrosis and chronic obstructive pulmonary disease.

According to the present invention, the terms "individual" or "patient" are used interchangeably to refer to a member of mammalian specie, preferably a human.

According to the present invention the term "antibacterial" means reducing the harmful effects of bacteria by inhibiting, suppressing the growth and/or killing them.

According to the present invention the term "bactericidal" means having a destructive killing action upon bacteria.

According to the present invention, "bacterial infection" refers to any situation in which the presence of a microbial population(s) is damaging to a host mammal. Thus, an individual is "suffering" from a microbial infection when excessive numbers of a microbial population are present in or on an individual's body, or when the effects of the presence of a microbial population(s) is damaging the cells or other tissue of an individual.

According to the present invention, the term "exacerbation(s)" refers to an increase in the severity of a disease or any of its signs or symptoms. In particular, pulmonary exacerbations can be identified with intermittent episodes of acute worsening of the patient's respiratory symptoms that are beyond day-to-day variations and lead to a change in medication and often cause morbidity, hospital admissions, mortality and strongly influence health-related quality of life.

According to the present invention, the term "treat" or "treating" refers to a diminution, a decrease, an attenuation, a limitation, or a mitigation of the degree, intensity, extent of a bacterial infection or its related symptoms caused by a susceptible strain of BCC and *S. maltophilia* in individuals suffering of a chronic disease impacting also the lower respiratory system.

NAC is commercially available and may also be synthesized by methods known in the art.

The pharmaceutical compositions comprising NAC for use according to the present invention together with a carrier suitable for pharmaceutical use consisting of one or more excipients is also encompassed by the scope of the present invention.

According to the present invention, the term "carrier" comprises any substance suitable as a vehicle for delivering NAC to a suitable in vivo or in vitro site.

According to the present invention, the term "excipient" comprises any inert substance added to a pharmaceutical composition to further facilitate administration of an active ingredient.

Any suitable route of administration may be used for the compositions of the present invention, including oral, parenteral (subcutaneous, intramuscular or intravenous) and inhalation route.

According to the present invention, the terms "oral" or "orally" refer to the introduction into the body by mouth whereby absorption occurs in one or more of the following areas of the body: the mouth, stomach, small intestine, and the small blood vessels of the oral mucosa.

Non-limiting examples of NAC formulations for oral administration include, for example, tablets, coated tablets, granulates, pills, capsules, liquids, gels, syrups, suspensions, and the like, for oral ingestion by an individual. Suitable carriers for oral administration are well known in the art.

For parenteral administration, NAC may be formulated in aqueous solutions, for example in physiologically compatible buffers or physiological salt buffer. Formulations for injection may be presented in unit dosage forms, for example, in ampoules, or in multi-dose containers with, optionally, an added preservative.

For administration by inhalation route, NAC may be typically formulated in aqueous solutions and conveniently delivered as fine nebulae by using conventional nebulizers made of plastic or glass, so that optimal quantities of a suitable range of particle sizes are provided to the patient. NAC may be also administered via direct instillation into the lower airways by intratracheal or mucosal administration; or direct instillation of NAC may be carried out with an intrapulmonary aerosolizer or a sub-miniature aerosolizer.

Pharmaceutical compositions of the present invention may be manufactured in conventional manners, following processes well known in the art.

Preferred pharmaceutical compositions according to the present invention are tablets and vials.

The amount of NAC for use according to the present invention may vary depending on the administration route, the selected kind of composition, the individual characteristics of the patient, the duration of the treatment and the nature of concurrent therapies.

For example, the effective amount of NAC can produce a diminution, a decrease, an attenuation, a limitation, or a mitigation of the degree, intensity, extent of a bacterial infection or its related symptoms caused by a susceptible strain of BCC and *S. maltophilia* in individuals suffering of a chronic disease impacting also the lower respiratory system such as, e.g. cystic fibrosis and chronic obstructive pulmonary disease.

In a particular aspect, the effective amount of NAC can reduce the frequency, duration or mitigate/attenuate/reduce the severity of episodes of pulmonary exacerbations caused at least in part by a susceptible strain of BCC and *S. maltophilia*, in an individual suffering of a chronic disease impacting also the lower respiratory system, such as, e.g. cystic fibrosis and chronic obstructive pulmonary disease, and/or speed time to symptomatic improvement of said episodes.

According to one embodiment, the effective amount of NAC may vary between 100 and 5800 mg/day to be administered in a single dose or in more repeated doses. Preferably, the effective amount of NAC may vary between 100 and 4600 mg/day.

Different dosage forms containing NAC for different indications are commercially available in the European Union and the United States. Pharmaceutical compositions comprising NAC are sold, for example, in Italy under the trademark FLUIMUCIL®.

The exact composition, route of administration, and dosage can be chosen by the individual physician in view of the patient's condition.

For better illustrating the invention the following non-limiting example is now given.

EXAMPLE

Material/methods: Minimal Inhibitory Concentrations (MICs) of NAC against 16 *S. maltophilia* and 16 BCC (i.e. *B. cepacia, B. cenocepacia, B. multivorans, B. metallica, B. seminalis, B. stabilis*) clinical isolates were determined by the broth microdilution method. The antimicrobial and anti-biofilm activity of NAC was further investigated with eight selected strains (4 *S. maltophilia* and 4 BCC isolates) exhibiting an MIC of 16 mg/ml. The antimicrobial activity was evaluated by monitoring the effect of sub-MIC concentrations (i.e. 4 and 8 mg/ml) on growth curves, and by performing time-kill assays (at 16 and 32 mg/ml). The ability of NAC in inhibiting biofilm formation (at 4, 8 and 16 mg/ml) was investigated using the MBEC High-Throughput Assay, and evaluated by viable cell count (VCC).

Results: MICs of NAC were 16 mg/ml for nine and seven isolates of *S. maltophilia* and BCC, respectively, and 32 mg/ml for the remaining ones. At sub-MIC concentrations, NAC slowed down the growth of all tested isolates. In time-kill assays, NAC at 32 mg/ml was bactericidal (i.e. a caused a reduction of bacterial inoculum by more than 3 logs) against one *S. maltophilia* and one BCC isolate, and accounted for a reduction ranging from 1.1 to 1.7 log CFU/ml with three additional isolates (two *S. maltophilia* and one BCC), while a reduction of <1 log CFU/ml was observed with the remaining ones. Biofilm growth ranged from 6.7 to 7.1 log CFU/peg and from 5.1 to 6.6 log CFU/peg for *S. maltophilia* and BCC, respectively. NAC was found to inhibit biofilm formation in a dose-dependent fashion with all *S. maltophilia* and two BCC isolates. The $\Delta$ log CFU/peg, compared to control, ranged from 0.75 to 3.8 log CFU/peg and from 2.5 to 5.8 log CFU/peg at NAC 8 mg/ml and NAC 16 mg/ml, respectively.

In conclusion, NAC showed intrinsic antimicrobial activity against BCC and *S. maltophilia* strains. Besides inhibiting the growth at NAC concentrations $\geq 16$ mg/ml, and slowing down the growth rates at sub-MIC concentrations, NAC was also found to exert some killing activity against BCC and *S. maltophilia*, sometimes achieving a bactericidal effect (i.e. conventionally defined as reduction of bacterial inoculum by more than 3 logs). Strikingly, NAC also showed a promising efficacy in preventing biofilm formation by those pathogens.

The invention claimed is:

1. A method of preventing lung colonization by *Burkholderia* cepacian complex (BCC) in individuals affected by chronic diseases impacting lower respiratory system by inhibiting biofilm formation caused by said BCC, said method comprising
   administering a pharmaceutically effective amount of a pharmaceutical composition comprising NAC to said individuals,
   wherein said pharmaceutical composition is administered orally, parenterally, by inhalation, nebulization or instillation.

2. The method according to claim 1, wherein the chronic disease is cystic fibrosis or chronic obstructive pulmonary disease.

3. The method according to claim 2, wherein individuals suffering from a chronic disease are immunocompromised and/or hospitalized patients.

4. The method according to claim 1, wherein said pharmacological effective amount varies between 10 and 5800 mg/day.

5. The method according to claim 1, wherein said pharmacological effective amount varies between 100 and 4600 mg/day.

6. The method according to claim 1, wherein said pharmacological effective amount is administered in a single dose or in more repeated doses.

7. The method according to claim 1, wherein said BCC grow in said biofilm.

8. A method of preventing lung colonization by BCC in individuals affected by chronic diseases impacting lower respiratory system by inhibiting biofilm formation caused by said BCC, said method comprising
   administering a pharmaceutically effective amount of a pharmaceutical composition comprising NAC and at least one pharmaceutically acceptable carrier and/or excipient to said individuals, wherein said pharmaceutical composition is administered orally, parenterally, by inhalation, nebulization or instillation.

9. A method of inhibiting biofilm formation during BCC infection caused by said BCC in individuals affected by chronic diseases impacting lower respiratory system, said method comprising:
   administering a pharmaceutically effective amount of a pharmaceutical composition comprising NAC to said individuals, wherein said pharmaceutical composition is administered orally, parenterally, by inhalation, nebulization or instillation.

* * * * *